United States Patent
Platteeuw et al.

(10) Patent No.: US 9,987,287 B2
(45) Date of Patent: Jun. 5, 2018

(54) ORALLY DISINTEGRATING SOLID DOSAGE UNIT CONTAINING AN ESTETROL COMPONENT

(71) Applicant: Donesta Bioscience B.V., Zeist (NL)

(72) Inventors: Johannes Jan Platteeuw, Boxtel (NL); Herman Jan Tijmen Coelingh Bennink, Zeist (NL)

(73) Assignee: Donesta Bioscience B.V., Zeist (NL)

( * ) Notice: Subject to any disclaimer, the term of this patent is extended or adjusted under 35 U.S.C. 154(b) by 0 days. days.

(21) Appl. No.: 15/852,187

(22) Filed: Dec. 22, 2017

(65) Prior Publication Data

US 2018/0117063 A1    May 3, 2018

Related U.S. Application Data

(62) Division of application No. 15/103,180, filed as application No. PCT/EP2014/077127 on Dec. 10, 2014, now Pat. No. 9,884,064.

(30) Foreign Application Priority Data

Dec. 12, 2013   (EP) .................................. 13196904

(51) Int. Cl.
| | |
|---|---|
| *A61K 31/565* | (2006.01) |
| *A61K 31/573* | (2006.01) |
| *A61K 9/16* | (2006.01) |
| *A61K 9/00* | (2006.01) |

(52) U.S. Cl.
CPC .......... *A61K 31/565* (2013.01); *A61K 9/0056* (2013.01); *A61K 9/1623* (2013.01); *A61K 9/1682* (2013.01); *A61K 31/573* (2013.01)

(58) Field of Classification Search
None
See application file for complete search history.

(56) References Cited

U.S. PATENT DOCUMENTS

| | | |
|---|---|---|
| 6,117,446 A | 9/2000 | Place |
| 2004/0198671 A1 | 10/2004 | Bunschoten et al. |
| 2007/0048369 A1 | 3/2007 | Foreman et al. |
| 2007/0286819 A1 | 12/2007 | Devries et al. |
| 2007/0286829 A1 | 12/2007 | Batista |

FOREIGN PATENT DOCUMENTS

| | | |
|---|---|---|
| WO | WO-02/094275 A1 | 11/2002 |
| WO | WO-02/094276 A1 | 11/2002 |
| WO | WO-02/094278 A1 | 11/2002 |
| WO | WO-02/094279 A1 | 11/2002 |
| WO | WO-03/018026 A1 | 3/2003 |
| WO | WO-03/041718 M | 5/2003 |
| WO | WO-2007/081206 | 7/2007 |
| WO | WO-2008/156365 | 12/2008 |
| WO | WO-2010/033832 A2 | 3/2010 |
| WO | WO-2014/159377 A1 | 10/2014 |

OTHER PUBLICATIONS

Coelingh Bennink et al., "Ovulation inhibition by estetrol in an in vivo model" Contraception, 2008, vol. 77, pp. 186-190.
International Search Report issued in International Patent Application No. PCT/EP2014/077127, dated Feb. 3, 2015.

*Primary Examiner* — Jessica Worsham
(74) *Attorney, Agent, or Firm* — Gilberto M. Villacorta; Sunit Talapatra; Foley & Lardner LLP

(57) ABSTRACT

The present invention provides an orally disintegrating solid pharmaceutical dosage unit having a weight of 50-1,000 mg and containing at least 0.1 mg of an estetrol component selected from estetrol, estetrol esters and combinations thereof. This solid dosage unit consists of:
  4-95 wt. % of granules consisting of:
    3-80 wt. % of an estetrol component selected from estetrol, estetrol esters and combinations thereof;
    20-97 wt. % $C_4$-$C_{12}$ sugar alcohol;
    0-45 wt. % of one or more other pharmaceutically acceptable ingredients; and
  5-96 wt. % of one or more pharmaceutically acceptable excipients.

The solid dosage units of the present invention are particularly suited for sublingual, buccal or sublabial administration of the estetrol component.

13 Claims, 4 Drawing Sheets

Figure 1a – mannitol
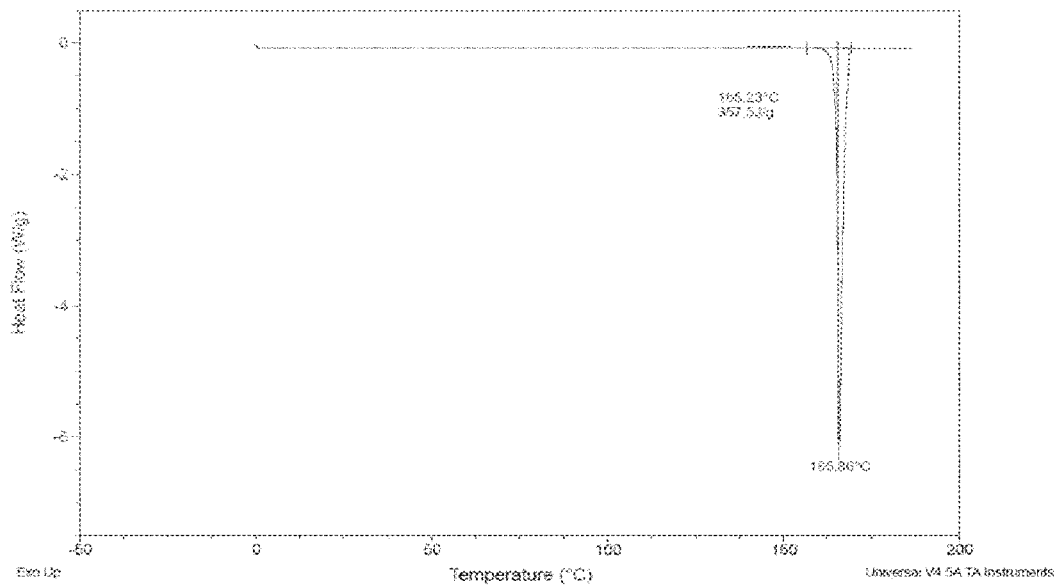
Figure 1b – estetrol monohydrate
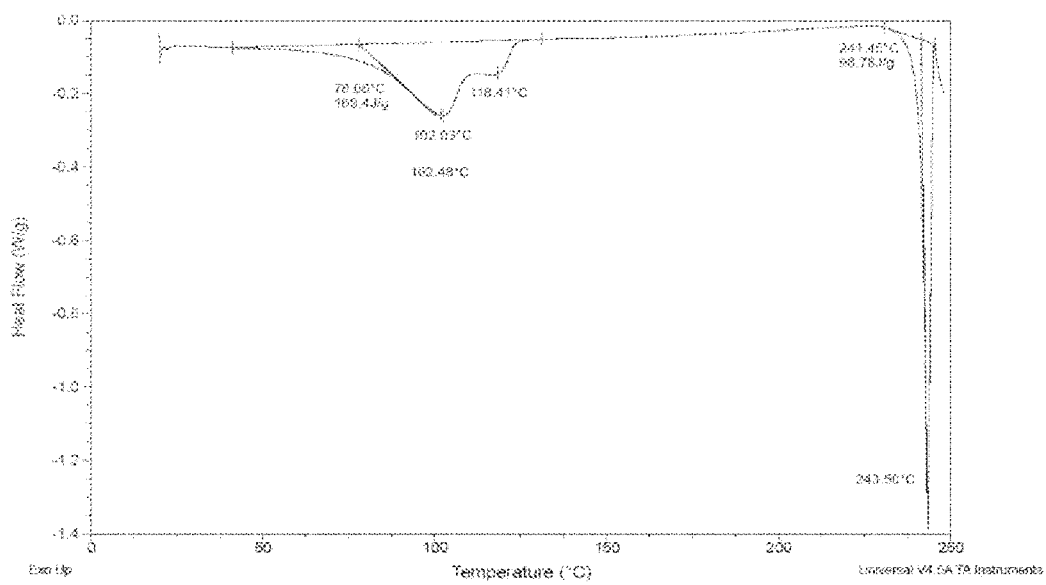

Figure 1c – granules Example 1
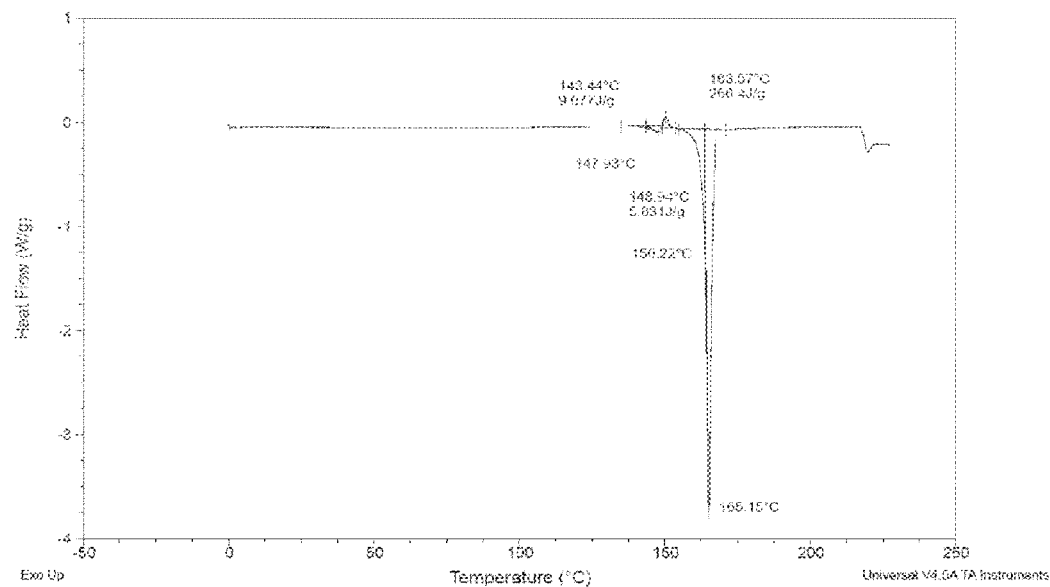
Figure 1d – granules Example 2
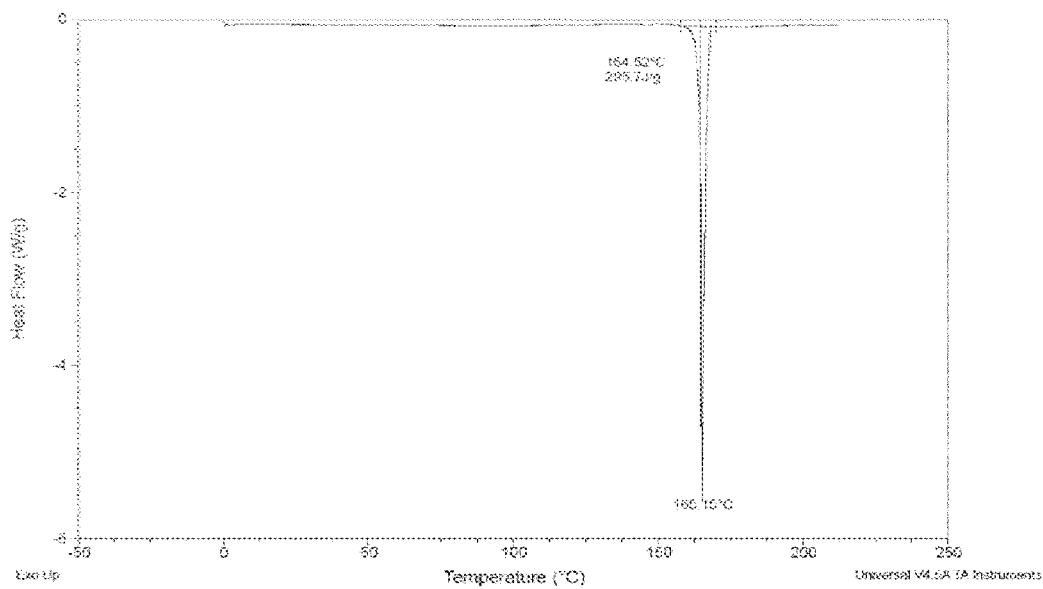

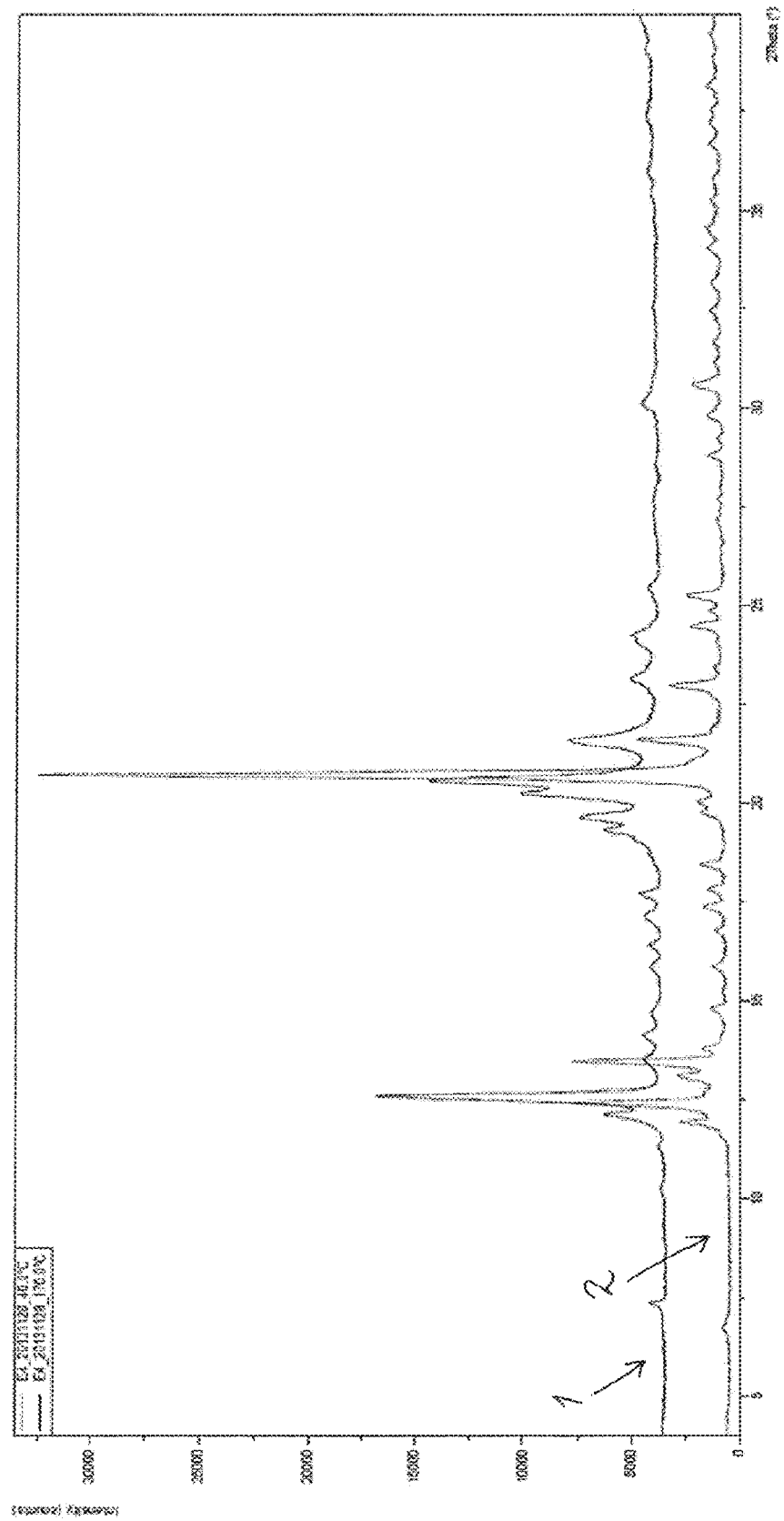

ORALLY DISINTEGRATING SOLID DOSAGE UNIT CONTAINING AN ESTETROL COMPONENT

CROSS-REFERENCE TO RELATED APPLICATIONS

This application is a Division of U.S. patent application Ser. No. 15/103,180, filed Jun. 9, 2016, which is the National Phase of International Patent Application No. PCT/EP2014/077127, filed Dec. 10, 2014, published on Jun. 18, 2015 as WO 2015/086643 A1, which claims priority to European Patent Application No. 13196904.0, filed Dec. 12, 2013. The contents of these applications are herein incorporated by reference in their entirety.

TECHNICAL FIELD OF THE INVENTION

The present invention provides an orally disintegrating solid pharmaceutical dosage unit having a weight of 50-1,000 mg and containing at least 0.1 mg of an estetrol component selected from estetrol, estetrol esters and combinations thereof. This solid dosage unit consists of:
  4-95 wt. % of granules consisting of:
    3-80 wt. % of an estetrol component selected from estetrol, estetrol esters and combinations thereof;
    20-97 wt. % $C_4$-$C_{12}$ sugar alcohol;
    0-45 wt. % of one or more other pharmaceutically acceptable ingredients; and
  5-96 wt. % of one or more pharmaceutically acceptable excipients.

The solid dosage units of the present invention are particularly suited for sublingual, buccal or sublabial administration of the estetrol component.

The invention also provides a method of preparing the aforementioned solid dosage unit.

BACKGROUND OF THE INVENTION

Estetrol is a human steroid, produced by the fetal liver during pregnancy only. This natural hormone was discovered in urine of pregnant women by Diczfalusy and coworkers in 1965. Estetrol has the structure of an estrogenic steroid with four hydroxyl groups. Estetrol is synthesized in the fetal liver from estradiol and estriol by the two enzymes 15α- and 16α-hydroxylase. After birth the neonatal liver rapidly loses its capacity to synthesize estetrol because these two enzymes are no longer expressed.

Estetrol reaches the maternal circulation through the placenta and was already detected at nine weeks of pregnancy in maternal urine. During the second trimester of pregnancy high levels were found in maternal plasma, with steadily rising concentrations of unconjugated estetrol to about 1 ng/mL (>3 nmol/L) towards the end of pregnancy. So far the physiological function of estetrol is unknown. The possible use of estetrol as a marker for fetal well-being has been studied quite extensively. However, due to the large intra- and inter-individual variation of maternal estetrol plasma levels during pregnancy this appeared not to be feasible.

Since 2001 estetrol has been studied extensively. In humans estetrol was shown to have a high and dose-proportional oral bioavailability and a long terminal elimination half-life of about 28 hours. Results from in vitro studies showed that estetrol binds highly selective to the estrogen receptors with preference for the ERα form of the receptor, unlike the estrogens ethinyl estradiol and 17β-estradiol. Also in contrast with ethinyl estradiol and especially with 17β-estradiol, estetrol does not bind to sex hormone binding globulin (SHBG) and does not stimulate the production of SHBG in vitro.

The properties of estetrol have also been investigated in a series of predictive, well validated pharmacological in vivo rat models. In these models, estetrol exhibited estrogenic effects on the vagina, the uterus (both myometrium and endometrium), body weight, bone mass, bone strength, hot flushes and on ovulation (inhibition). All these effects of estetrol were dose-dependent with maximum effects at comparable dose levels. Surprisingly, estetrol prevented tumour development in a DMBA mammary tumour model to an extent and at a dose level similar to the anti-estrogen tamoxifen and to ovariectomy. This anti-estrogenic effect of estetrol in the presence of 17β-estradiol has also been observed in in vitro studies using human breast cancer cells.

Buccal, sublingual or sublabial administration of estetrol is mentioned in a number of patent applications, including WO 2002/0894275, WO 2002/094276, WO 2002/094278 and WO 2003/018026. Estetrol containing dosage units for buccal, sublingual or sublabial administration are not described in these publications.

WO 2010/033832 describes an oral dosage form comprising an estriol compound and a pharmaceutically acceptable matrix material, wherein the oral dosage form releases at least about 90% of the estriol compound in a time of less than about 300 seconds when contacted with saliva of the buccal and/or sublingual cavity.

U.S. Pat. No. 6,117,446 describes a buccal dosage unit for administering a combination of steroidal active agents, comprising a compressed tablet of a bioerodible polymeric carrier and therapeutically effective amounts of an androgenic agent selected from testosterone and pharmacologically acceptable esters thereof, a progestin and an estrogen. The examples describe buccal dosage units that were prepared by thoroughly mixing the following components: estrogen, progestogen, androgen, polyethylene oxide, carbomer and magnesium stearate. Next, the mixture was granulated by means of fluid bed granulation and the granulate so obtained was pressed into tablets.

Oral dosage units containing estetrol have been described in several patent publications.

WO 2002/094276 describes a pharmaceutical composition for use in a method of hormone replacement therapy, which method comprises administering to a person in need of such a therapy an effective amount of estetrol, said composition containing virtually no progestogen or anti-progestin. WO 2002/094276 describes the preparation of estetrol tablets having a weight of 185 mg, containing 1.5 mg estetrol, on the basis of the following formulation:

|  | mg |
| --- | --- |
| Estetrol | 1.5 |
| Polyvinylpyrrolidone (Kollidon 25 ® ex BASF) | 12.5 |
| Lactose | 135.795 |
| Microcrystalline cellulose (Avicel PH 101 ®) | 26.25 |
| Glyceryl palmitostearate (Precirol ®) | 2.775 |
| Anhydrous colloidal silica (Aerosil 200 ®) | 1.0 |
| Crospovidone (Polyplasdone XL ®) | 4.0 |
| Coloring agent | 0.18 |

WO 2002/094275 describes the use of an estetrol in a method of increasing libido in a woman, said method comprising administering to said woman an effective amount of estetrol. Oral administration is mentioned as a suitable mode of administration. This patent application describes the same estetrol tablet as WO 2002/094276.

WO 2002/094279 describes the use of estetrol in a method of contraception in mammalian females, which method comprises the oral administration of said estrogenic component and a progestogenic component to a female of childbearing capability in an effective amount to inhibit ovulation. The following formulation for a 185 mg estetrol tablet is described in this international patent application.

|  | Mg |
| --- | --- |
| Estetrol | 1.5 |
| Levonorgestrel | 0.15 |
| Polyvinylpyrrolidone (Kollidon 25 ® ex BASF) | 13.5 |
| Lactose | 135.645 |
| Microcrystalline cellulose (Avicel PH 101 ®) | 26.25 |
| Glyceryl palmitostearate (Precirol ®) | 2.775 |
| Anhydrous colloidal silica (Aerosil 200 ®) | 1.0 |
| Crospovidone (Polyplasdone XL ®) | 4.0 |
| Coloring agent | 0.18 |

WO 2003/041718 describes the use of estetrol in a method of hormone replacement in mammals, which method comprises the oral administration of estetrol and a progestogenic component to a mammal in an effective amount to prevent or treat symptoms of hypoestrogenism. This patent application describes the same estetrol tablet as WO 2002/094279.

WO 2007/081206 describes the use of estetrol in a method of treating an acute vascular disorder in a mammal, said method comprising orally administering to said mammal, upon demand, an effective amount of the estetrol to the mammal. This patent application describes the preparation of hard gelatine capsules, containing 100 mg estetrol and 25 mg sildenafil citrate per capsule.

WO 2008/156365 describes the use of estetrol in the treatment of Meconium Aspiration Syndrome (MAS) in a newborn infant, said treatment comprising administering an effective amount of estrogen to said newborn infant within 7 days after birth. The international patent application describes a suppository for use in newborn infants comprising at least 1 µg of estrogen, said suppository further being characterized by a maximum diameter of less than 10 mm and a weight of less than 0.5 g. The excipient contained in the suppository may be based on lipid material that melts at body temperature or it may be based on a hydrophilic component that dissolves or disintegrates when it comes into contact with water.

SUMMARY OF THE INVENTION

The present invention provides an orally disintegrating solid pharmaceutical dosage unit containing an estetrol component. The dosage unit comprises a high load of the estetetrol component and rapidly releases the estetrol in aqueous environment. The solid dosage unit is easy to manufacture and perfectly suited for sublingual, buccal or sublabial administration. Sublingual, buccal and sublabial administration each offer the advantages that the estetrol component does not have to pass through the digestive system and avoids first-pass liver exposure.

The solid dosage unit according to the present invention has a weight between 50 and 1,000 mg and consists of:
4-95 wt. % of granules consisting of:
3-80 wt. % of an estetrol component selected from estetrol, estetrol esters and combinations thereof;
20-97 wt. % $C_4$-$C_{12}$ sugar alcohol;
0-45 wt. % of one or more other pharmaceutically acceptable ingredients;
5-96 wt. % of one or more pharmaceutically acceptable excipients;
the solid dosage unit comprising at least 0.1 mg of the estetrol component.

Rapid and complete dissolution of the estetrol component into saliva is essential for efficient delivery of the component via sublingual, buccal or sublabial administration of the solid dosage unit. Although the inventors do not wish to be bound by theory it is believed that the granules containing the estetrol component and the sugar alcohol contribute to the efficient release of the estetrol component into saliva during sublingual, buccal or sublabial administration. When coming into contact with saliva, the excipients or the dosage unit rapidly dissolve, thereby releasing the granules containing the estetrol component the sugar alcohol. These granules, once released, rapidly disintegrate thanks to the water-solubility of the sugar alcohol, thereby allowing the estetrol component to become dispersed into the saliva. Subsequently, the estetrol component is swiftly absorbed through mucosal tissue within the oral cavity and will enter the blood circulation.

The invention also provides a method of preparing the aforementioned solid dosage unit, said method comprising the steps of:
providing a hot pumpable mixture of the estetrol component, the $C_4$-$C_{12}$ sugar alcohol and the optional one or more other pharmaceutically acceptable ingredients, said hot pumpable mixture having a temperature of at least 105° C.;
cooling down the hot pumpable mixture to solidify $C_4$-$C_{12}$ sugar alcohol and breaking up the pumpable mixture prior to or after said cooling to produce solid granules;
mixing the granules with the one or more pharmaceutically acceptable excipients; and
forming the mixture into a solid dosage unit.

BRIEF DESCRIPTION OF THE FIGURES

FIGS. 1a, 1b, 1c and 1d depict differential scanning calorimetry (DSC) curves that were obtained for two different estetrol and manittol containing granules, for estetrol monohydrate and for mannitol.

FIG. 3 shows the diffraction patterns that were obtained when estetrol monohydrate was subjected to x-ray powder diffraction analysis at 40° C. and 170° C.

DETAILED DESCRIPTION OF THE INVENTION

Figure 2:
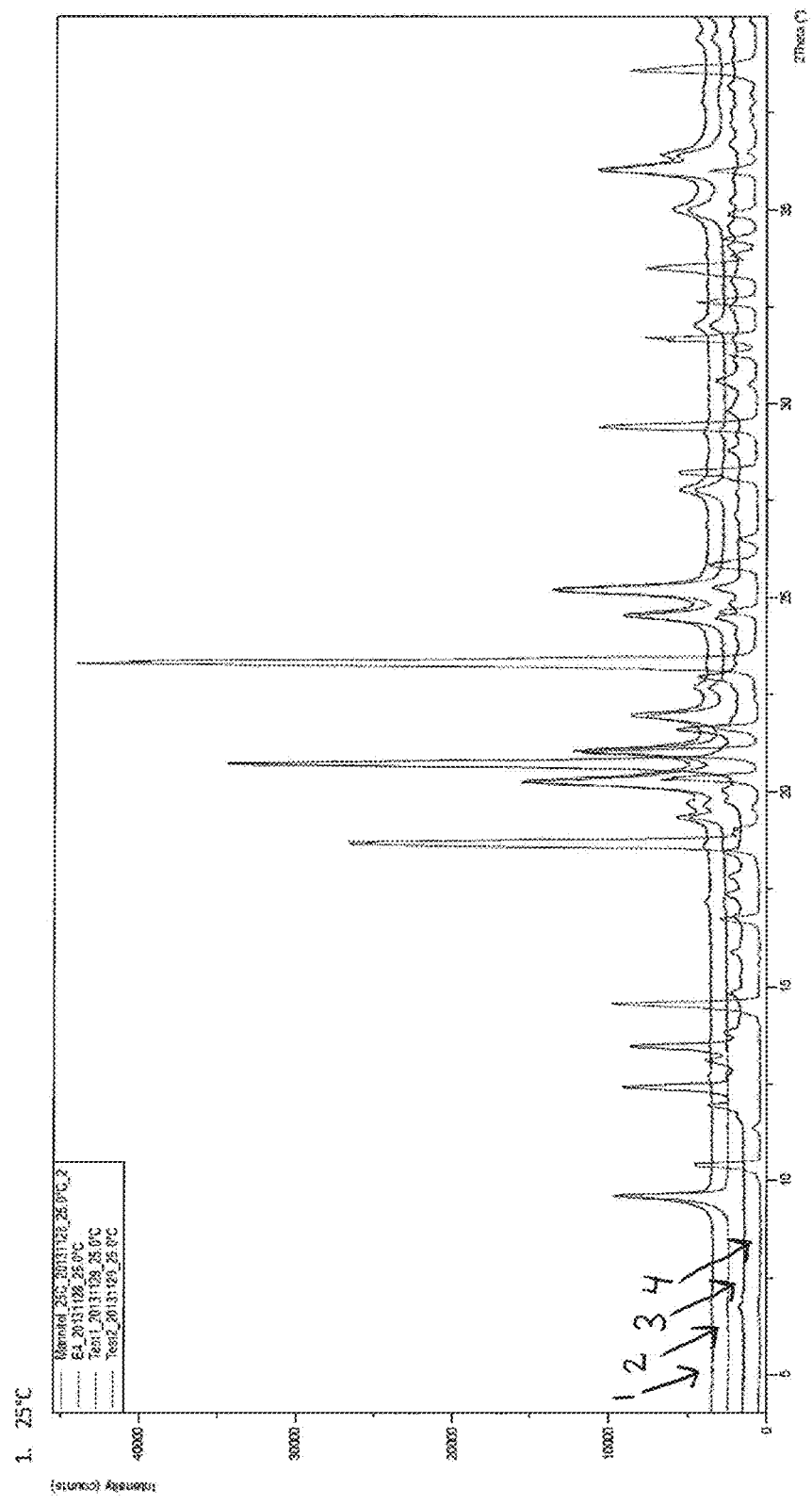
FIG. 2 shows the diffraction patterns that were obtained when each of the aforementioned granules, estetrol monohydrate and mannitol were subjected to x-ray powder diffraction analysis at 25° C.

A first aspect of the invention relates to an orally disintegrating solid pharmaceutical dosage unit having a weight between 50 and 1,000 mg, said dosage unit consisting of:
4-95 wt. % of granules consisting of:
3-80 wt. % of an estetrol component selected from estetrol, estetrol esters and combinations thereof;
20-97 wt. % $C_4$-$C_{12}$ sugar alcohol;

0-45 wt. % of one or more other pharmaceutically acceptable ingredients;

5-96 wt. % of one or more pharmaceutically acceptable excipients;

the solid dosage unit comprising at least 0.1 mg of the estetrol component.

The term 'estetrol' as used herein refers to 1,3,5 (10)-estratrien-3,15α,16α,17β-tetrol or 15α-hydroxyestriol as well as hydrates of estetrol, e.g. estetrol monohydrate.

The term 'granule' as used herein refers to a particle having a diameter in the range of 20 to 500 μm. When assessing the diameter of granules within the solid dosage unit, it should be understood that the granules may be in direct contact with one another, especially if the dosage unit has been prepared by, for instance, compression.

The term 'sugar alcohol' as used herein refers to a polyol having the general formula $H(HCHO)_nH$ or $C_6H_{11}O_6$—$CH_2$—$(HCHO)_oH$. Most sugar alcohols have five- or six carbon chains, because they are derived from pentoses (five-carbon sugars) and hexoses (six-carbon sugars), respectively. Other sugar alcohols may be derived from disaccharides and typically contain eleven or twelve carbon atoms. Examples of sugar alcohols containing 12 carbon atoms include glucose mannitol and glucose sorbitol. Erythritol is a naturally occurring sugar that contains only four carbon atoms.

The term 'sublingual' as used herein refers to the pharmacological route of administration by which the estetrol component diffuses into the blood through tissues under the tongue.

The term 'buccal' as used herein refers to the pharmacological route of administration by which the estetrol component diffuses into the blood through tissues of the buccal vestibule, the area inside the mouth between the lining of cheek (the buccal mucosa) and the teeth/gums.

The term 'sublabial' as used herein refers to the pharmacological route of administration by which the estetrol component is placed between the lip and the gingiva.

The term 'solid dispersion' as used herein refers to compositions containing estetrol component dispersed or dissolved within a solid carrier matrix. Different types of solid dispersions can be distinguished on the basis of the physical form of the estetrol component and the carrier. The estetrol component is either suspended in the carrier as phase-separated crystalline or amorphous particles, or it exists as a homogeneous molecular mixture of (amorphous) drug and carrier. The carrier can exist in amorphous or crystalline form. More information on solid dispersions can be found in Williams et al., Strategies to Address Low Drug Solubility in Discovery and Development, Pharmacological Reviews (2013) 65, 416-445.

Examples of solid dosage units encompassed by the present invention include tablets, dragees, lozenges and films. In accordance with a preferred embodiment, the dosage unit is a tablet, most preferably a compressed tablet.

The solid dosage unit typically has a weight between 60 and 900 mg, more preferably between 75 and 750 mg, and most preferably between 100 and 500 mg.

The solid dosage unit of the present invention offers the advantage that the estetrol component is rapidly released when the dosage unit is introduced into the oral cavity and comes into contact with saliva. The rate of release of the estetrol component from the dosage unit can suitably be determined using the dissolution test described in the Examples. The solid dosage unit of the present invention, when subjected to the aforementioned dissolution test, typically releases at least 50%, more preferably at least 70% and most preferably at least 80% of the estetrol component after 5 minutes.

The granules containing the estetrol component and the sugar alcohol typically represent between 5-90 wt. % of the dosage unit. More preferably, said granules represent 8-75 wt. %, most preferably 10-50 wt. % of the dosage unit.

The granules containing the estetrol component and the sugar alcohol preferably have a volume weighted average size between 30 and 200 μm, more preferably between 40 and 150 μm and most preferably between 50 and 120 μm.

The granules typically contain between 5 and 50 wt. %, more preferably between 6 and 30 wt. % and most preferably between 7 and 25 wt. % of the estetrol component.

The $C_4$-$C_{12}$ sugar alcohol is typically contained in the granules in a concentration of 30-95 wt. %, more preferably of 50-94 wt. % and most preferably of 75-93 wt. %.

Release of the estetrol component from the granules into saliva is expedited if the granules contain at least 50 wt. %, more preferably at least 65 wt. % and most preferably at least 75 wt. % of a water-soluble, crystalline matrix.

The solid dosage unit preferably comprises at least 1 wt. %, more preferably 2-40 wt. % and most preferably 2.2-15 wt. % of the estetrol-component.

The amount of the estetrol component contained in the solid dosage unit preferably lies within the range of 0.3-100 mg, more preferably of 0.5-40 mg and most preferably of 1-20 mg.

The estetrol component of the present invention preferably is selected from the group consisting of estetrol, esters of estetrol wherein the hydrogen atom of at least one of the hydroxyl groups has been substituted by an acyl radical of a hydrocarbon carboxylic, sulfonic acid or sulfamic acid of 1-25 carbon atoms; and combinations thereof. Even more preferably, the estetrol component is estetrol (including estetrol hydrates). Most preferably, the estetrol component is anhydrous estetrol.

Anhydrous estetrol offers the advantage that it dissolves more rapidly into saliva than estetrol monohydrate. This is particularly true for crystalline anhydrous estetrol which dissolves significantly more rapidly into saliva than crystalline estetrol monohydrate.

Anhydrous estetrol is highly hygroscopic. The inventors have discovered, however, that the anhydrous estetrol that is contained in the granules of the solid dosage unit of the present invention is highly stable, i.e. it remains anhydrous even if the dosage unit is left in direct contact with atmospheric air for several weeks.

The estetrol component is preferably contained in the granules in crystalline form.

According to a particularly preferred embodiment, the granules comprise a solid dispersion of the estetrol component in a matrix containing the $C_4$-$C_{12}$ sugar alcohol. Typically, the dispersed phase containing the estetrol component has a volume weighted average diameter of less than 5 μm, more preferably of less than 500 nm and most preferably of less than 250 nm.

The estetrol containing granules preferably contain a $C_4$-$C_{12}$ sugar alcohol selected from mannitol, erythritol, isomalt and combinations thereof. Even more preferably, the sugar alcohol is selected from mannitol, erythritol and combinations thereof. Most preferably, the sugar alcohol is mannitol.

$C_4$-$C_{12}$ sugar alcohol is preferably contained in the granules in crystalline form, The estetrol component and the $C_4$-$C_{12}$ sugar alcohol are typically contained in the granules in a weight ratio that lies within the range of 1:1 to 1:50, more preferably of 2:3 to 1:25 and most preferably of 1:2 to 1:10.

Besides the estetrol component and the $C_4$-$C_{12}$ sugar alcohol the granules may contain one or more other pharmaceutically acceptable ingredients. Examples of such other pharmaceutically acceptable ingredients include steroid hormones (other than the estetrol component), vitamins, disintegrating agents, muco-adhesive agents, fillers, and combinations thereof. Typically, the one or more other pharmaceutically acceptable ingredients represent not more than 30 wt. %, more preferably not more than 15 wt. % and most preferably not more than 5 wt. % of the granules.

The solid dosage unit of the present invention preferably contains 0.05-10 mg, more preferably 0.1-5 mg of one or more progestogens, preferably one or more progestogens selected from progesterone, levonorgestrel, norgestimate, norethisterone, norethisteron-acetate (NETA), dydrogesterone, drospirenone, 3-beta-hydroxydesogestrel, 3-keto desogestrel (=etonogestrel), 17-deacetyl norgestimate, 19-norprogesterone, acetoxypregnenolone, allylestrenol, anagestone, chlormadinone, cyproterone, demegestone, desogestrel, dienogest, dihydrogesterone, dimethisterone, ethisterone, ethynodiol diacetate, flurogestone acetate, gastrinon, gestodene, gestrinone, hydroxymethylprogesterone, hydroxyprogesterone, lynestrenol (=lynoestrenol), medrogestone, medroxyprogesterone, megestrol, melengestrol, nestorone, nomegestrol, nomegestrol-acetate (NOMAC), norethindrone (=norethisterone), norethynodrel, norgestrel (includes d-norgestrel and dl-norgestrel), norgestrienone, normethisterone, progesterone, quingestanol, (17alpha)-17-hydroxy-11-methylene-19-norpregna-4,15-diene-20-yn-3-one, tibolone, trimegestone, algestone acetophenide, nestorone, promegestone, 17-hydroxyprogesterone esters, 19-nor-17hydroxyprogesterone, 17alpha-ethinyl-testosterone, 17alpha-ethinyl-19-nor-testosterone, d-17beta-acetoxy-13beta-ethyl-17alpha-ethinyl-gon-4-en-3-one oxime and prodrugs of these compounds. Preferably the one or more progestogens used in accordance with the present invention is selected from the group consisting of progesterone, desogestrel, etonogestrel, gestodene, dienogest, levonorgestrel, norgestimate, norethisterone, norethisteron-acetate (NETA), nomegestrol, nomegestrol-acetate (NOMAC), drospirenone, trimegestone, nestorone and dydrogesterone.

The solid dosage unit according to the present invention preferably contains 0.05-100 mg, more preferably 0.1-50 mg of one or more androgens, preferably one or more androgens selected from testosterone, dehydroepiandrosterone (DHEA); DHEA-sulphate (DHEAS); testosterone esters (e.g. testosterone undecanoate, testosterone propionate, testosterone phenylpropionate, testosterone isohexanoate, testosterone enantate, testosterone bucanate, testosterone decanoate, testosterone buciclate); methyltestosterone; mesterolon; stanozolol; androstenedione; dihydrotestosterone; androstanediol; metenolon; fluoxymesterone; oxymesterone; methandrostenolol; MENT and prodrugs of these compounds. Most preferably the one or more androgens are selected from the group consisting of testosterone, DHEA and MENT.

The one or more other pharmaceutically acceptable excipients that are combined with the granules in the solid dosage unit are preferably include one or more of the following excipients: $C_4$-$C_{12}$ sugar alcohol, crospovidone, (low-substituted) hydroxypropyl cellulose, croscarmellose sodium, microcrystalline cellulose lactose, pregelatined starch, sodium starch glycolate, sodium lauryl sulphate and combinations thereof. According to a particularly preferred embodiment, the aforementioned excipients together constitute at least 50 wt. %, more preferably at least 80 wt. % and most preferably at least 85 wt. % of the one or more pharmaceutically acceptable excipients.

According to a particularly preferred embodiment, the one or more pharmaceutically acceptable excipients that are contained in the solid dosage units besides the granules containing the estetrol components also contain a substantial amount of $C_4$-$C_6$ sugar alcohol. Advantageously, $C_4$-$C_6$ sugar alcohol represents 20-90 wt. %, more preferably 30-70 wt. and most preferably 35-65 wt. % of said one or more pharmaceutically acceptable excipients.

The latter $C_4$-$C_6$ sugar alcohols are preferably selected from mannitol, xylitol and combinations thereof. According to a particularly preferred embodiment, mannitol represents 15-70 wt. %, most preferably 25-60 wt. % of the one or more pharmaceutically acceptable excipients that are contained in the solid dosage units besides the granules According to another preferred embodiment, the solid dosage unit contains 5.50 wt. %, more preferably 8-40 wt. % and most preferably 10-30 wt. % of a disintegrating agent selected from crospovidone, low-substituted hydroxypropyl cellulose, croscarmellose sodium and crystalline cellulose and combinations thereof. According to a particularly preferred embodiment, the disintegrating agent is selected from crospovidone, crystalline cellulose and combinations thereof.

The one or more pharmaceutically acceptable excipients that are contained in the solid dosage units besides the granules containing the estetrol components preferably include at least 30%, more preferably at least 50% by weight of said one or more pharmaceutically acceptable excipients of particles containing a disintegrating agent dispersed in a matrix containing $C_4$-$C_6$ sugar alcohol. Preferably, these particles contain 10-50 wt. % of the disintegrating agent and 40-90 wt. % of the $C_4$-$C_6$ sugar alcohol. Even more preferably, the aforementioned particles contain 10-50 wt. % of the disintegrating agent and 40-85 wt. % of mannitol. The aforementioned particles typically have a volume weighted mean particle size of 50-300 μm, most preferably of 70-200 μm. F-Melt® (Fuji Chemical Industry Co.) is an example of a commercially available particulate material that contains a disintegrating agent dispersed in a matrix containing $C_4$-$C_6$ sugar alcohol (mannitol and xylitol). Ludiflash® (BASF) is another example of a commercially available particulate material that contains a disintegrating agent dispersed in a matrix of $C_4$-$C_6$ sugar alcohol (mannitol).

Another aspect of the present invention relates to the use of the aforementioned solid dosage unit in medical treatment, in female hormone replacement therapy or in female contraception, said use comprising sublingual, buccal or sublabial administration of the dosage unit. Examples of medical treatment in which the solid dosage unit of the present invention may suitably be used include treatment of osteoporosis and estrogen add-back treatment in endometriosis, breast cancer or prostate cancer. In accordance with a preferred embodiment, the solid dosage unit is used in female hormone replacement therapy or female contraception. Most preferably, the solid dosage is used in female hormone replacement therapy, especially to treat vulvovaginal atrophy and/or vasomotor symptoms.

To treat vulvovaginal atrophy the dosage unit is preferably administered in an amount sufficient to provide at least 0.05 mg of the estetrol component. More preferably, the administered dosage unit provides at least 0.1 mg, most preferably at least 0.2 mg of the estetrol component. In the treatment of vulvovaginal atrophy the dosage unit is preferably administered in an amount that provides no more than 5 mg, more preferably not more than 2 mg and most preferably not more than 1 mg of the estetrol component.

To treat vasomotor symptoms the dosage unit is preferably administered in an amount sufficient to provide at least 1 mg of the estetrol component. More preferably, the administered dosage unit provides at least 2 mg, most preferably of at least 5 mg of the estetrol component. In the treatment of vasomotor symptoms the dosage unit is preferably administered in an amount that provides no more than 100 mg, more preferably not more than 40 mg and most preferably not more than 20 mg of the estetrol component.

Typically, these uses of the solid dosage unit comprise once daily administration of the dosage unit during a period of at least 1 week, more preferably of at least 2 weeks. During these periods the solid dosage unit is preferably administered to provide a daily dose of at least 0.05 mg, more preferably of 0.1-40 mg and most preferably of 0.2-20 mg of the estetrol component.

To treat vulvovaginal atrophy the dosage unit is preferably administered to provide a daily dose of at least 0.05 mg of the estetrol component. More preferably, the dosage unit is administered to provide a daily dose of 0.1-5 mg, most preferably of 0.2-2 mg of the estetrol component.

To treat vasomotor symptoms the dosage unit is preferably administered to provide a daily dose of at least 1 mg of the estetrol component. More preferably, the dosage unit is administered to provide a daily dose of 2-20 mg, most preferably 5-40 mg of the estetrol component.

Yet another aspect of the invention relates to a method of preparing the solid dosage unit as described herein before, said method comprising the steps of:
- providing a hot pumpable mixture of the estetrol component, the $C_4$-$C_{12}$ sugar alcohol and the optional one or more other pharmaceutically acceptable ingredients, said hot pumpable mixture having a temperature of at least 105° C.;
- cooling down the hot pumpable mixture to solidify $C_4$-$C_{12}$ sugar alcohol and breaking up the pumpable mixture prior to or after said cooling to produce solid granules;
- mixing the granules with the one or more pharmaceutically acceptable excipients; and
- forming the mixture into a solid dosage unit.

The estetrol component employed in the present method preferably is estetrol (including estetrol hydrates). Even more preferably the estetrol component is selected from anhydrous estetrol and estetrol monohydrate. Most preferably, the estetrol component is estetrol monohydrate.

The inventors have unexpectedly discovered that the present method enables the preparation of a solid dosage unit containing anhydrous estetrol, starting from estetrol monohydrate. It is believed that in the preparation of the hot pumpable mixture at elevated temperature estetrol monohydrate is dehydrated to its anhydrous form.

The $C_4$-$C_{12}$ sugar alcohol employed in the preparation method preferably is selected from mannitol, erythritol, isomalt and combinations thereof. Even more preferably, said sugar alcohol is elected from mannitol, erythritol and combinations thereof. Most preferably, the sugar alcohol is mannitol.

The hot pumpable mixture may suitably be prepared by heating a blend containing the estetrol component and the $C_4$-$C_{12}$ sugar alcohol to a temperature above the melting point of the $C_4$-$C_{12}$ sugar alcohol, e.g. to a temperature of at least 160° C., more preferably of at least 170° C. and most preferably of at least 180° C.

Alternatively, the $C_4$-$C_{12}$ sugar alcohol may heated to a temperature above the melting point of said sugar alcohol (e.g. to a temperature of at least 160° C., preferably of at least 170° C. and most preferably of at least 180° C.), following which the estetrol component is added to the sugar alcohol.

The hot pumpable mixture typically has a temperature of at least 160° C., more preferably of at least 170° C. and most preferably of at least 180° C.

According to a particularly preferred embodiment, the temperature of the hot pumpable mixture containing the estetrol component is maintained below the melting point of the estetrol component. Typically, the temperature of the hot pumpable mixture is maintained below 240° C., more preferably below 230° C. and most preferably below 225° C.

The hot pumpable mixture is preferably thoroughly mixed in order to homogeneously disperse the estetrol component as very fine particles throughout the molten sugar alcohol.

According to a particularly preferred embodiment of the present method, the hot pumpable mixture is subjected to spray chilling to produce the solid granules. Here the term "spray chilling" refers to a procedure in which the pumpable mixture is sprayed into a cold atmosphere and/or onto a cold surface and wherein heat transfer from the spray particles to the cold atmosphere and/or the cold surface causes these particles to solidify.

The forming of the mixture of granules and one or more pharmaceutically acceptable excipients into a solid dosage unit preferably comprises compaction of this mixture.

Compactibility is the ability of a powder bed to form a mechanically strong tablet; whereas the compressibility is the ability of a powder bed to be compressed and consequently be reduced in volume. Compaction as applicable to a pharmaceutical powder consists of the simultaneous processes of compression and consolidation of a two-phase (particulate solid-gas) system due to an applied force. Consolidation refers to the increase in the mechanical strength of a material as a result of particle/particle interactions.

The solid dosage units obtained by the present method can packaged in different ways. Preferably, the dosage units are packaged in a blister pack containing at least 14 dosage units.

The invention is further illustrated by means of the following non-limiting examples.

EXAMPLES

Example 1

Tablets containing 2.5 wt. % of estetrol were prepared by the method described below.

Mannitol (melting point 168° C.) was heated with the help of a heating bath to 200° C. Estetrol monohydrate powder (mass weighted average diameter 75 μm) was gradually added to the molten mannitol under stirring until the mixture contained estetrol and mannitol in a weight ratio of 1:5.

The molten mixture was introduced into a spray chiller (ProCept R&D Spray dryer) at a rate of 3 g/min. Cooling air having a temperature of 5° C. was simultaneously introduced at a rate of 500 l/min. The molten mixture was introduced into the spray chiller through a bi-fluid nozzle having an internal diameter of 1.2 mm, using a nozzle air flow of 4.7 l/min.

The granulate so obtained had a mass weighted average diameter of approximately 100 μm.

A tabletting mixture was prepared using the aforementioned mannitol-estetrol granulate on the basis of the recipe shown in Table 1.

TABLE 1

| Ingredient | Amount (in grams) | Wt. % |
|---|---|---|
| Mannitol-estetrol (5:1) granulate | 5.00 | 15.00 |
| Prosolv ® HD 90 (Silicified Microcrystalline Cellulose) | 3.33 | 10.00 |
| Pruv ® (sodium stearyl fumarate) | 0.16 | 0.48 |
| Ac-Di-sol ® (croscarmellose sodium) | 1.65 | 4.95 |
| Aspartame | 0.16 | 0.48 |
| Lime flavour | 0.08 | 0.24 |
| F-melt ® (excipient)[1] | 22.95 | 68.86 |

[1]containing mannitol, xylitol, microcrystalline cellulose and crospovidone

The granulate and excipients were mixed for 15 minutes in a free-fall mixer before being compressed into tablets of 100 mg using an Excenter press. Each tablet contained 2.5 mg of estetrol.

HPLC analyses of the tablets showed levels of impurities in the tablets to be very low.

Example 2

Tablets containing 2.49 wt. % of estetrol were prepared by the method described below.

A granulate containing estetrol and mannitol in a weight ratio of 1:10 was prepared by the procedure described in Example 1.

A tabletting mixture was prepared using the aforementioned granulate on the basis the recipe shown in Table 2.

TABLE 2

| Ingredient | Amount (in grams) | Wt. % |
|---|---|---|
| Mannitol-estetrol (10:1) granulate | 5.00 | 27.38 |
| Prosolv ® HD 90 (Silicified Microcrystalline Cellulose) | 1.81 | 9.91 |
| Pruv ® (sodium stearyl fumarate) | 0.10 | 0.55 |
| Ac-Di-sol ® (croscarmellose sodium) | 1.00 | 5.48 |
| Aspartame | 0.10 | 0.55 |
| Lime flavour | 0.05 | 0.27 |
| F-melt ® (excipient) | 10.20 | 55.86 |

The granulate and excipients were mixed for 15 minutes in a free-fall mixer before being compressed into tablets of 100 mg using an Excenter press. Each tablet contained approximately 2.5 mg of estetrol.

HPLC analyses of the tablets showed levels of impurities in the tablets to be very low.

Example 3

The tablets of Example 1 were subjected to the dissolution test described below.

Dissolution Apparatus
  Paddle and basket dissolution tester VanKel VK 7010 or VK 7025, autosampler VK 8000, 1000 mL dissolution vessels and porous micron filters (35 pin)

Dissolution Medium
  Transfer 9,000 ml of demineralised water into a volumetric flask of 10,000 ml.
  Add 68.05 g of $KH_2PO_4$ and 8.96 g NaOH and stir the solution until everything is dissolved.
  Mix the solution and adjust the pH to 6.8 with NaOH or phosphoric acid, if necessary and make up to volume with demineralised water.

Dissolution Procedure
  Transfer 900 ml of Dissolution Medium into each vessel of the paddle apparatus.
  Assemble the apparatus, warm the medium to 37±0.5° C., and remove the thermometer.
  Place in each of the six vessels one tablet at the bottom before starting the rotation of the paddles.
  Start the rotation of the paddles immediately.
  Use a stirring speed of 50 rpm.
  Take samples of 5 ml from the dissolution vessels after 5, 10, 20, 30, 45, 60, 75 and 90 minutes for a complete dissolution profile. Take the sample from a position midway between the surface of the dissolution medium and the top of the paddle blade and not less than 10 mm from the vessel wall. The removed dissolution volume is not replaced by fresh dissolution medium.

Estetrol concentrations in the samples were determined by means of HPLC using estetrol stock solutions as a reference.

Preparation of Mobile Phase (MP) Phosphate Buffer
  Transfer 1.15 g of $NH_4H_2PO_4$ (10 mM) into a 1,000 ml of demineralised water, dissolve it and adjust the pH to 3.0 with phosphoric acid.

HPLC Apparatus
  Alliance 2695 Separations module consisting of a quaternary solvent delivery system, a variable volume injector, a temperature controlled autosampler, column thermostat and Photodiode array detector 2996 (all by Waters)
  Analytical column: Symmetry C18, 3.9×150 mm, dp=5 µm (ex Waters)
  Guard column: Security guard column C18, 4×3 mm (Phenomenex)
  Flow: 1.0 mL/min
  Detection: UV@280 nm
  Column temperature: 30° C.
  Autosampler temperature: 10° C.
  Injection volume: 100
  Run time: 12 min

| Elution gradient | | |
|---|---|---|
| Time (min) | Acetonitrile (%) | Phosphate buffer (%) |
| 0 | 20 | 80 |
| 9 | 75 | 25 |
| 10 | 20 | 80 |
| 12 | 20 | 80 |

The dissolution tests were conducted in triplicate. The averaged results so obtained are shown in Table 3

TABLE 3

| Time (min.) | Average % |
|---|---|
| 0 | 0 |
| 5 | 79.8 |
| 10 | 86.7 |
| 20 | 89.4 |
| 30 | 89.9 |
| 45 | 89.5 |
| 60 | 89.6 |

TABLE 3-continued

| Time (min.) | Average % |
|---|---|
| 75 | 89.7 |
| 90 | 89.9 |

Example 4

The tablets of Example 2 were subjected to the dissolution test described in Example 3.

The dissolution tests were conducted in triplicate. The averaged results so obtained are shown in Table 4

TABLE 4

| Time (min.) | Average % |
|---|---|
| 0 | 0 |
| 5 | 106.8 |
| 10 | 109.1 |
| 20 | 109.8 |
| 30 | 110.1 |
| 45 | 110.0 |
| 60 | 109.8 |
| 75 | 109.6 |
| 90 | 109.7 |

Example 5

The granules containing estetrol and mannitol described in Examples 1 and 2 were analyzed by means of differential scanning calorimetry (DSC). Estetrol monohydrate and mannitol were subjected to the same DSC analysis. The results of these DSC analyses are shown in FIGS. 1a to 1d.

The DSC curve for estetrol monohydrate (FIG. 1b) shows that dehydration of estetrol monohydrate occurred between 70 and 125° C., followed by melting of the anhydrous estetrol around 241.5° C. The anhydrous estetrol decomposed upon melting.

From these figures it can be concluded that mannitol is present in the granules in crystalline form and that estetrol is present in anhydrous crystalline form.

Example 6

The granules of Examples 1 and 2, estetrol monohydrate as well as mannitol were subjected to x-ray powder diffraction analysis at 25° C. The results are shown in FIG. 2. The diffraction patterns of the granules of Examples 1 and 2 are depicted as patterns 2 and 1, respectively. The diffraction patterns of estetrol monohydrate and mannitol are depicted as patterns 3 and 4, respectively.

In addition, estetrol monohydrate was subjected to x-ray powder diffraction analysis at 40° C. and 170° C. The results are shown in FIG. 3. The diffraction pattern obtained at 40° C. corresponds to pattern 2. The diffraction pattern obtained at 170° C. corresponds to pattern 1.

All of the samples showed Bragg peaks indicating crystallinity of the samples.

The diffractogram of mannitol is that of the beta-polymorph.

The diffractograms of the granules of Examples 1 and 2 show Bragg peaks which are different from those of the estetrol monohydrate and that of the mannitol, indicating the formation of a different phase (crystal form) during or after spray chilling.

The diffractograms of estetrol monohydrate at 40° C. and 170° C. indicate that a different crystal structure is formed upon dehydration of the monohydrate at higher temperatures.

Example 7

Tablets of 200 mg containing 10 mg of estetrol were prepared by the method described below.

Mannitol (melting point 168° C.) was heated with the help of a heating bath to 200° C. Estetrol monohydrate powder (mass weighted average diameter 75 μm) was gradually added to the molten mannitol under stirring until the mixture contained estetrol and mannitol in a weight ratio of 1:9.

The molten mixture was introduced into a spray chiller (ProCept R&D Spray dryer) at a rate of 15 g/min. Cooling air having a temperature of 5° C. was simultaneously introduced at a rate of 250 l/min. The molten mixture was introduced into the spray chiller through a bi-fluid nozzle having an internal diameter of 1.2 mm, using a nozzle air flow of 7 l/min.

The granulate so obtained had a mass weighted average diameter of approximately 90 μm.

A tabletting mixture was prepared using the aforementioned mannitol-estetrol granulate on the basis of the tablet recipe shown in Table 5.

TABLE 5

| Ingredient | Grams | Wt. % |
|---|---|---|
| Mannitol-estetrol (9:1) granulate | 600 | 49.5 |
| SuperTab 11SD[1] | 120 | 9.9 |
| Sodium stearyl fumarate | 18 | 1.5 |
| Ludiflash ®[2] | 474 | 39.1 |

[1]Spray dried lactose (ex DFE Pharma)
[2]Containing mannitol (90 wt. %), crospovidone (5 wt. %) and polyvinyl acetate (5 wt. %)

The granulate and excipients were mixed for 15 minutes at 15 rpm in a V-blender. Next, the mixture was sieved over a 800 μm Retsch sieve. After sieving, the blend was transferred again to the V-blender and mixed again at 15 rpm for 15 minutes.

The blend was subsequently compressed on a Korsch XP1 single punch tablet press using a round shaped punch with 6.5 mm diameter and 0.26 punch cup depth. The filling depth was adjusted to result in a 200 mg tablet weight. The speed was set at 30 strokes per minute. The blend was compressed using varying different compression forces. An overview of the tabletting settings is given in Table 6.

TABLE 6

| Batch | Upper position (mm) | Lower position (mm) | Compression force (kN) | | Ejection force (kN) |
|---|---|---|---|---|---|
| | | | Upper punch | Lower punch | |
| 1 | 5.65 | 9.39 | 5.0 | 4.8 | 235 |
| 2 | 5.99 | 9.39 | 10.2 | 9.1 | 300, | friability and disintegration time of the tablets so obtained were determined in accordance with the protocols described in European Pharmacopoeia, 8th ed.

The results of these measurements are shown in Table 7

TABLE 7

| Batch | Resistance to | | Disintegration time | |
|---|---|---|---|---|
| | crushing | Friability | Water | 0.1N HCl |
| 1 | 46N | 0.4% | 52 sec. | 31 sec. |
| 2 | 90.N | 0.1% | 205 sec. | 166 sec. |

Example 8

A randomized, open-label, single dose, two-period, crossover, pharmacokinetic study is conducted to compare sublingual bioavailability of 10 mg estetrol administered in two 100 mg tablets (each containing 5 mg estetrol and having the same composition as the tablets described in Example 7) with oral availability of estetrol contained in a 83 mg tablet containing 10 mg estetrol. These tablets are administered sublingually and orally to healthy female postmenopausal volunteers under fasting conditions.

Twelve healthy postmenopausal female subjects are selected on the basis of the following criteria: Caucasian race, age of 45-65 years (inclusive), nonsmokers or past smokers (at least 6 months before dosing), body-mass index (BMI)=18.5 to 30 kg/m² (inclusive at the time of the screening).

At the start of the first and the second period of the study, between 07:00 am and 07:28 am, 6 subjects receive a single dose of the sublingual formulation of estetrol by administering two estetrol tablets (tablet weight 100 mg; 5 mg estetrol each) and 6 subjects receive a single oral dose of the oral estetrol formulation by administering one estetrol tablet (tablet weight 83 mg; 10 mg estetrol), ingested together with 200 ml water.

Subjects are required to fast for at least 10 hours prior to tablet administration and for at least 4 hours after administration. Drinking of water or beverages is not permitted within 1 hour before the drug administration. Subjects receive 200 ml of water 1 hour prior to and 2 hours after tablet administration. Subjects are free to drink water and fruit tea from 4 hours following the tablet administration. Standardized meals are provided 10.5 hours before and 4, 6, 9, and 13 hours after tablet administration.

The sequence of events that occurs during the first and second period is shown in Table 8:

TABLE 8

| Event | |
|---|---|
| First period | |
| Day 1 | Confinement from 19:00 |
| Day 2 | Dosing, blood and urine sampling, confinement |
| Day 3 | Exit procedure, confinement till 8 am |
| Days 4-8 | Return visits |
| Days 9-13 | Wash out |
| Second period | |
| Day 14 | Confinement from 19:00 |
| Day 15 | Dosing, blood and urine sampling, confinement |
| Day 16 | Exit procedure, confinement till 8 am |
| Days 17-21 | Return visits |
| Days 22-26 | Wash out |
| Day 27 | Intramuscular injection of 200 mg progesterone |
| Day 28 | Phone call, progestin withdrawal test check |

The blood and urine sampling schedule used in this study is shown in Table 9.

TABLE 9

| Blood sampling | Blood collection (4 ml) is performed prior to administration of the tablet (0), and subsequently 0:10, 0:15, 0:20, 0:25, 0:30, 0:35, 0:40, 0:45, 0:50, 0:55, 1:00, 1:10, 1:20, 1:30, 2, 3, 4, 6, 10, 16, 24, 48, 72, 96, 120, 144 hours after administration. Total number of blood collections in each period is 27. |
|---|---|
| Urine sampling | Urine collection is performed prior to administration of the tablet and 2, 4, 8, 12, 24, 48, 72, 96, 120 and 144 hours after administration. Total number of urine collections in each period is 11. |

The estetrol concentration in the collected blood samples is determined by means of HPLC/MS/MS. The concentrations of glucuronided estetrol (D-ring) in the urine samples is also determined with the help of HPLC/MS/MS.

Results of these analyses show that the bioavailability of sublingually administered estetrol is comparable or even superior to orally administered estetrol. Furthermore, the data suggest that sublingually administered estetrol has an earlier bioavailability compared to orally administered estetrol. Sublingual estetrol has less impact on a liver function parameter

The invention claimed is:
1. A method for contraception, comprising administering to a mammalian female sublingually, buccally or sublabially an orally disintegrating solid pharmaceutical dosage unit having a weight between 50 and 1,000 mg, the dosage unit consisting of:
(a) 4-95 wt. % of granules consisting of:
(i) 3-80 wt. % of an estetrol component selected from estetrol, estetrol esters and combinations thereof;
(ii) 20-97 wt. % $C_4$-$C_{12}$ sugar alcohol; and
(iii) 0-45 wt. % of one or more pharmaceutically acceptable ingredients; and
(b) 5-96 wt. % of one or more pharmaceutically acceptable excipients;
wherein the solid dosage unit has at least 0.1 mg of the estetrol component.
2. The method according to claim 1, wherein the administering is once daily administration.
3. The method according to claim 1, wherein the estetrol component is estetrol.
4. The method according to claim 3, wherein the estetrol is anhydrous estetrol.
5. The method according to claim 1, wherein the dosage unit consists of 5 to 90 wt. % of the granules.
6. The method according to claim 1, wherein the granules have a volume weighted average size between 30 and 200 µm.
7. The method according to claim 1, wherein the granules have a volume weighted average size between 40 and 150 µm.
8. The method according to claim 1, wherein the $C_4$-$C_{12}$ sugar alcohol is selected from mannitol, erythritol, isomalt and combinations thereof.
9. The method according to claim 1, wherein the one or more pharmaceutically acceptable excipients of (b) comprise particles containing a disintegrating agent dispersed in a matrix containing a $C_4$-$C_6$ sugar alcohol, wherein the particles represent at least 30 wt. % of the one or more pharmaceutically acceptable excipients.

10. The method according to claim 9, wherein the particles have 10-50 wt. % of disintegrating agent and 40-90 wt. % of $C_4$-$C_6$ sugar alcohol.

11. The method according to claim 10, wherein the disintegrating agent is selected from crospovidone, hydroxypropyl cellulose, croscarmellose sodium, crystalline cellulose and combinations thereof.

12. The method according to claim 9, wherein the $C_4$-$C_6$ sugar alcohol is selected from mannitol, xylitol and combinations thereof.

13. The method according to claim 1, wherein the pharmaceutically acceptable ingredient comprises progestogen present in an amount of 0.05-10 mg.

* * * * *